(12) United States Patent
Shah et al.

(10) Patent No.: US 6,955,805 B2
(45) Date of Patent: Oct. 18, 2005

(54) NON-TACKY MASCARA COMPOSITION

(75) Inventors: Amit R. Shah, Commack, NY (US); Nicole B. Huggins, Westbury, NY (US); Janet Pardo, New York, NY (US)

(73) Assignee: Color Access, Inc., New York, NY (US)

( * ) Notice: Subject to any disclaimer, the term of this patent is extended or adjusted under 35 U.S.C. 154(b) by 100 days.

(21) Appl. No.: 09/324,182

(22) Filed: Jun. 2, 1999

(65) Prior Publication Data

US 2002/0102226 A1 Aug. 1, 2002

(51) Int. Cl.⁷ .................................................. A61K 7/02
(52) U.S. Cl. ...................... 424/70.7; 424/725; 424/765
(58) Field of Search ................................ 424/70.7, 725, 424/765, 401

(56) References Cited

U.S. PATENT DOCUMENTS

| | | |
|---|---|---|
| 4,029,727 A | 6/1977 | Austin et al. |
| 4,820,510 A | 4/1989 | Arraudeau et al. |
| 4,822,598 A | 4/1989 | Lang et al. |
| 5,552,135 A | 9/1996 | Cioca et al. |
| 5,601,810 A | 2/1997 | Mausner |
| 5,874,092 A | 2/1999 | Roulier et al. |

FOREIGN PATENT DOCUMENTS

| | | |
|---|---|---|
| EP | 0 781 544 | 7/1997 |
| FR | 2 770 776 | 5/1995 |
| GB | 2 321 061 | 7/1998 |
| GB | 2 321 644 | 8/1998 |
| JP | 5170629 | 7/1993 |
| JP | 7179323 | 7/1995 |
| SU | 1486167 | 6/1989 |
| SU | 1776407 | 11/1992 |
| SU | 1782590 | 12/1992 |

OTHER PUBLICATIONS

International Search Report PCT/US 00/15095, 2 pgs (Nov. 3, 2000).

*Primary Examiner*—Jyothsna Venkat
(74) *Attorney, Agent, or Firm*—Karen A. Lowney; Dorene M. Price

(57) ABSTRACT

The invention relates to mascara compositions comprising a plant extract, especially, an apple extract component dispersed in a silicone oil. These mascaras can also contain a fiber component unrelated to the fiber content of the fruit extract. The fiber component, when it is charged, is capable of aligning itself with the natural direction of the eyelashes when an antistatic component is also present. The mascaras contain a natural ingredient of apple extract and are not tacky.

29 Claims, No Drawings ion to the eyelashes. More specifically, the invention
NON-TACKY MASCARA COMPOSITION

FIELD OF THE INVENTION

The invention relates to a cosmetic composition for application to the eyelashes. More specifically, the invention relates to a non-tacky mascara composition containing a natural plant extract dispersed in a silicone oil.

BACKGROUND OF THE INVENTION

Many efforts have been made in the field of cosmetics to make them more natural as there has been, for some time now, a general trend by consumers to purchase products of any kind that are safer for the environment and for themselves. Consumers look for products that are in fact or are, at least, perceived to be natural. Typically, a product is deemed to be natural when it uses ingredients that are found and retrieved from nature with a minimal amount of processing or intervention by man to incorporate the ingredient into the product. As a result, the cosmetic industry has responded to this increased demand by using alternative natural ingredients to achieve desirable properties and features in cosmetic products. For example, waxes such as beeswax, carnauba, and polymers such as rosin are used in cosmetics.

Mascara is traditionally a challenging cosmetic product due to the features that consumers desire. Some of the features that consumers expect a mascara to have include the ability to thicken and lengthen lashes while still allowing the eyelashes to look natural, and therefore, consumers desire a mascara that will resist smudging and flaking. In addition to being smudge-proof, it is desirable for mascara to be water resistant and transfer resistant (i.e., resist unwanted removal while remaining easy to remove when desired). Further, as the mascara is applied to the eyelashes in close proximity to the sensitive eye and certainly in the sensitive eye area, the mascara should not cause allergic reactions. And, there is even a desire for the mascara to promote healthy eyelashes by making them softer and smoother, and promoting their growth. To achieve this, typically natural conditioners, such as for example, lanolin or bisabolol or synthetic conditioners, like glycols or vitamin E, are added to the mascara. The ideal mascara should beautify the eye by enhancing the appearance of the eyelashes around the eye.

However, because of the various properties that a mascara is expected to have, to date, the potential to make a mascara containing natural ingredients has not been fulfilled. Formulating mascara compositions to include natural ingredients presents a challenge because many of the desired features of the mascara are lost or are at a minimum compromised when these types of ingredients are used. For example, the mascara does not apply easily, or is sticky and tacky because of the tendency of natural ingredients to gel when formulated in a mascara. And, although, consumers desire the use of natural ingredients, consumers still expect the mascara to meet certain performance standards.

In EP 781544, incorporated herein by reference, a cosmetic is disclosed which contains a polyphenol derived from the fruit of Rosaceae and preferably from apples. The cosmetics have useful activities such as ultraviolet light absorbing activity and free radical eradicating activity. However, the polyphenol is separated from other beneficial fruit components and it is prepared in an alcoholic solution. This process, therefore, does not provide for use of the natural extract of the whole fruit dispersed in a silicone oil.

In GB 2321061, incorporated herein by reference, a shampoo and conditioner for the hair contains cupuacu pulp, juice or oil. However, it does not disclose a non-tacky mascara composition containing a plant extract dispersed in a silicone oil. Also disclosed, in U.S. Pat. No. 5,601,810, incorporated herein by reference, is a mascara composition containing a vegetable wax component of jasmine or rose wax. The vegetable wax component is not disclosed as contributing a fibrous content to the mascara. Thus, many of the fibers disclosed are synthetic and the natural fibers are not derived from the vegetable.

In addition, fruit pectins are known in the prior art to be gellants, as it is disclosed, for example, in U.S. Pat. No. 5,874,092, incorporated herein by reference. However, the ability to formulate a silicone based natural fruit or vegetable extract into a mascara that is not tacky, and is not hard to apply is not disclosed. Thus, it remains a challenge to formulate a mascara with a natural component derived from fruits or vegetables that is not tacky or sticky, and that adheres well to the lashes.

To incorporate natural plants into a cosmetic, extracts such as, for example, coffee extracts, flower extracts, berry and cherry extracts, barley extracts, oat extracts, pepper extracts are known to be used in cosmetic formulations. For example, JP 9155450 discloses hair dye compositions in which one of two agents, in the composition, is a plant extract and a silicone oil component contained in the agent. And a variety of face creams, massage creams, and lipsticks are disclosed, for example, in SU 1776407, SU 1782590, and SU 1486167 comprising various extracts and an additional silicone oil component. However, it is not disclosed to use a plant extract dispersed in a silicone oil, and further, its use in a mascara is not disclosed.

There continues to be a need to formulate natural cosmetic mascaras which achieve the desired functions associated with beautifying the eye. The present invention now provides a means by which a mascara user can use a mascara containing natural plant derived ingredients that is non-tacky and enhances and beautifies the eyelashes and the eyes.

SUMMARY OF THE INVENTION

The present invention relates to a mascara composition comprising a plant extract component such that the plant extract is dispersed in a silicone oil. The plant extract can be dispersed in a volatile or non-volatile silicone oil. Although the plant extract contains its own natural plant fibers, the mascara can also comprise a non-plant fiber component comprising nylon and chitin, and an antistatic component such as chitin for aligning all of the fibers in the mascara with the eyelashes. The composition is not tacky and produces longer, fuller, and natural looking lashes when applied as a mascara.

DETAILED DESCRIPTION OF THE INVENTION

Mascara compositions of the present invention are similar to presently known mascaras in that they incorporate the basic formulation elements of a mascara. However, a mascara composition is not presently known to comprise a plant extract component in which the plant extract is dispersed in a silicone oil. It has been surprisingly discovered that a mascara composition containing the plant extract as a natural ingredient is easy to apply to the lashes and adheres to the lashes without being too sticky or tacky. The mascara compositions of the present invention also leave the lashes looking longer, fuller, and natural (i.e., the lashes are not clumped together, and do not looked spiked or pointed). The plant extract component can be derived from a fruit or a vegetable or any other similar type of plant, especially fruits or vegetables that are tacky or sticky.

The plant extract, as used in the present specification, is prepared using the whole fruit or vegetable that is, for example, ground, liquefied, pressed or processed using similar methods such that the whole processed plant is dispersible in a silicone oil. Except for the seeds, no part of the plant is removed or separated from the extract (i.e., the constituents of the fruit or vegetable are not filtered). The whole pulp and skin of the fruit or vegetable are used. A separation procedure is typically employed when making a plant extract to remove constituents of the plant that are tacky or sticky. It has been discovered, however, that the present invention achieves a non-tacky mascara using an unfiltered plant extract dispersed in silicone oil. This has not been previously disclosed.

Examples of fruits, include but are not limited to, apples, pears, peaches, nectarines, mangoes, papayas, apricots, or any other type of fruit that can be made into an extract; and examples of vegetables, include but are not limited to, yams, potatoes, peas, beans, peppers, squashes, carrots, or any other type of vegetable that can be made into an extract. It is within the scope of the present invention to include combinations of fruits, combinations of vegetables, and combinations of fruits and vegetables. Preferably the plant extract is an apple extract.

The extract is dispersed in any cosmetically or pharmaceutically acceptable silicone oil. However, preferably a suitable volatile silicone oil is used. Suitable volatile silicone oils for use in the composition include, but are not limited to, both cyclic and linear silicones. Thus, cyclomethicones, such as for example, hexamethylcyclotrisiloxane, octamethylcyclotetrasiloxane, decamethylcyclopentasiloxane; and volatile linear dimethylpolysiloxane can be used. Non-volatile polymeric silicones such as dimethicone; alkylated derivatives of polymeric silicones such as cetyl dimethicone, phenyl trimethicone, or lauryl trimethicone; hydroxylated derivatives of polymeric silicones such as dimethiconol, or mixtures thereof can also be used. Preferably, the volatile silicone oil is cyclomethicone.

The extract dispersed in silicone oil is present in an amount of from about 0.05 to about 0.50 percent by weight of the composition, and preferably about 0.1 to about 0.4 percent by weight of the total composition. The plant extract can be dispersed in the silicone oil and then added as the extract component to the mascara composition, or alternatively, the plant extract component can be obtained premade with the extract already dispersed in the silicone oil. A predispersed apple extract in cyclomethicone, for example, is available commercially from Collaborative Laboratories, Inc. of East Setauket, N.Y.

The mascara compositions of the invention are easily used by the consumer. They are simply applied to the upper and/or the lower lashes and allowed to dry for about a minute or two. The resulting coat of mascara is smooth and non-tacky. The eyelashes are lengthened, separated, and have a natural appearance.

The plant extract also contributes natural plant derived fibers to the mascara as such fibers can be naturally present in the extract. These fibers include water soluble and insoluble fibers. In addition, the mascara can also comprise in combination with the plant derived fibers a non-plant fiber component which enhances the thickness of the eyelashes. Non-plant fibers include synthetic fibers and naturally occurring fibers from non-plant sources such as, for example, chitin. The addition of synthetic fibers to mascara is known in the art and is disclosed in, for example, JP 7179323, incorporated herein by reference. It is also known to include fibers, especially synthetic fibers, in cosmetic compositions in general, as disclosed in, for example, U.S. Pat. No. 4,820,510, also incorporated herein by reference. However, it is not disclosed in these references to make a mascara using plant derived fibers contained in a plant extract dispersed in a silicone oil. Accordingly, examples of synthetic fibers which can be combined with the plant fibers include, but are not limited to, nylon, polyester, polypropylene, polyethylene, acrylic, aramid, rayon, cotton, wool, silk, and blends thereof.

In a preferred embodiment, an antistatic component is present to align the fibers, both natural and synthetic, with the eyelashes and separate the eyelashes to render fuller, longer, and more natural-looking eyelashes. The antistatic component can be any kind that manipulates the fibers such that they align parallel with the direction of the natural eyelashes, and that is cosmetically or pharmaceutically acceptable for use around the eye. Examples of suitable antistatic agents include but are not limited to, surfactants such as nonionic, anionic, cationic, or amphoteric surfactants, in particular surfactants with quaternium groups. Preferably, mild surfactants are used such as LIPO-PEG-2DL or disodium cocoamphodiacetate (Miranol), or mixtures thereof. Other antistatic agents include polysaccharides such as chitin, and derivatives, such as, for example, etherified chitin, like carboxymethylated chitin and hydroxyethylated chitin, and esterified chitin, like acetylated chitin and sulfonated chitin, chitosan, quaternary chitosan, and derivatives such as, for example, carboxy methyl chitosan, sulfoethyl chitosan, and other derivatives thereof as disclosed in U.S. Pat. No. 4,822,598, incorporated herein by reference.

Preferably the antistatic component is a polysaccharide, more preferably the antistatic component is chitin. The antistatic component is present in an amount of from about 0.01 percent to about 10.00 percent by weight of the composition. Chitin, in its natural state, exists in small flakes or short fibrous material derived from the carapace or tendons of crustaceans. In addition, it is known in the art to prepare or regenerate fibers of chitin having tensile strength close to that of natural chitin, as disclosed in U.S. Pat. No. 4,029,727, incorporated herein by reference. The presence of chitin in the form of fibers, either natural or synthetic contributes to the fiber content of the compositions of the present invention. Chitin is also known to possess antimicrobial properties and may provide antimicrobial activity to the compositions of the present invention. In addition, some types of chitin such as that derived from squid, have a tendency to gel, in which case, the amount of chitin must not interfere with the smoothness and non-tackiness of the present invention achieved with the plant extract dispersed in silicone oil.

Another component of the mascara is a film-forming agent. The use of a film-former improves the wear of the mascara, and can confer transfer-resistance to the mascara. The film-forming agent may be any which is cosmetically acceptable for use around the eye. Examples of useful film-forming agents include natural waxes, polymers such as acrylic acid copolymers, polyethylene polymers, and copolymers of polyvinylpyrrolidone (PVP), ethylene vinyl acetate, dimethicone gum, and resins, such as shellac, polyterpenes, and various silicone resins, e.g., trimethylsiloxysilicate. Preferably, the film former is PVP and acrylic acid copolymer which produces a smooth, non-tacky film on the lashes. The film-former is used in an amount of from about 0.1 to about 50.0 percent, preferably from about 0.5 to about 20.0 percent by weight of the composition, more preferably 1.0 to 10.0 percent The mascara compositions of the invention may also comprise additional, optional components. For example, it may be desirable to add one or more preservatives or antioxidants to the formulation. Appropriate preservatives may include propyl paraben, butyl paraben, mixtures thereof, or isoforms thereof, as well as BHA or BHT.

The composition contains one or more pigments. Any pigment appropriate for use in the eye area may be used. Examples of useful pigments are metallic oxides, such as titanium or iron oxides, bismuth oxychloride, carmine, chromium oxide or chromium hydroxide greens, ultramarines, ferric ferrocyanide, ferric ammonium ferrocyanide, mica, FD&C blue No. 1, FD&C Red No.40, FD&C yellow No. 5, and FD&C green No. 5. Pigment will typically be used in an amount of up to about 20 percent, preferably at about 1 to about 10 percent by weight of the composition as a whole.

Other additional components are viscosifying agents such as waxes and other gellants, in an amount of from about 1 to about 30 percent by weight of the composition, preferably up to about 20 percent. The waxes may be any synthetic or natural waxes which are suitable for use in the eye area; preferably, the wax is plant-derived, for example, carnauba wax, candelilla wax, beeswax, synthetic wax, shellac wax, spermaceti, lanolin wax, ozokerite, bran wax, ceresin wax, bayberry wax, paraffin, rice wax and jojoba wax. Preferably the wax is beeswax.

The gellant may be, for example, bentone, triglycerides, aluminum stearate, $C_{18}$–$C_{36}$ acid glycol esters, glyceryl stearate, glyceryl tribehenate and the like. Other viscosifying agents include alginates, carbomers, celluloses, gums, carageenans, starches or silicates. The quantities of gellants and viscosifying agents, like the presence of some forms of chitin, must not alter the smoothness and non-tackiness of the plant extract dispersed in the silicone oil. Fillers can also optionally be added, in an amount of about 1 to about 20 percent by weight of the composition, preferably from about 1 to about 10 percent; these may be, for example, silica, PMMA, nylon, alumina, barium sulfate, talc or any other filler typically used in such compositions.

The invention is further illustrated by the following non-limiting examples:

EXAMPLES

Example 1

| Ingredient | % Amount |
| --- | --- |
| Phase I | |
| Purified Water | 40.80 |
| Simethicone | 0.15 |
| PVP | 3.00 |
| Methylparaben | 0.60 |
| Phase II | |
| Talc | 5.00 |
| Iron oxides | 10.00 |
| Phase III | |
| Nylon fiber | 1.25 |
| Phase IV | |
| Beeswax | 10.00 |

-continued

| Ingredient | % Amount |
| --- | --- |
| Ozokerite | 10.00 |
| Glyceryl stearate | 8.00 |
| Butylparaben | 0.20 |
| Propylparaben | 0.20 |
| Triclosan | 0.10 |
| Phase V | |
| Silicone Oil Based Apple Extract | 0.10 |
| Acrylates copolymer | 10.00 |
| Phase VII | |
| Phenoxyethanol | 0.50 |
| Phase VIII | |
| Chitin | 0.10 |

Add Phase I ingredients together and mix in a vessel until uniform at a temperature of 50° C. Add Phase II ingredients and Phase III ingredients and mix after addition of each. Combine Phase IV ingredients in a separate vessel and mix at a temperature of 80° C. When mixture is completely dissolved and clear, transfer mixture to vessel containing Phase I through III ingredients. Separately add the remaining Phase V, VI, VII and VIII ingredients in sequence and mix after adding each. Let cool to room temperature.

Example 2

A mascara composition containing apple extract, substantially described in Example 1, is prepared and tested. A study is conducted in cool and warm climates for a period of 27 days. In the cool climate, 51 panelists are selected from New Jersey, and in the warm climate, 47 panelists are selected from Florida. Thus, a total of 98 panelists, women ages 18 to 65 years old, are chosen. The panelists wear conventional mascara at least 5 days per week and desire lashes that appear longer. The panelists are instructed to use the mascara of the present invention at least once a day. They are permitted to apply the mascara as often as they deem it to be necessary and/or desirable. However, they are to apply the mascara as they would apply their normal mascara. To remove the mascara the panelists are to use soap and water or their normal eye makeup remover.

At the conclusion of the study, panelists complete a self-administered questionnaire. Results of the study indicate that 74% of panelists rate the mascara excellent/very good for being comfortable on the lashes and 87% find the mascara to be the same as or better than the mascara they use most often. With respect to a natural appearance, 41% of panelists rate the mascara excellent/very good and 90% find the appearance to be as natural as the brand they use most often. From the results of the study, 67% of the panelists also indicate that they find the mascara to be excellent/very good at not causing lashes to look spiked/pointed and 91% find it to be the same as or better than the mascara they use most often; 65% find that the mascara does not cause their lashes to clump together and 84% find that it does this the same as or better than the mascara they use most often; 62% find that the mascara lengthens the lashes and 70% find that it lengthens the same as or better than the brand they use most often, and 60% find that the mascara causes a separation of the lashes and 80% find that it performs better than the mascara they use most often. Therefore, this study demonstrates the ability of the mascara compositions containing a plant extract to be non-tacky and to produce longer, fuller, natural looking lashes the same as or better than that of conventional mascaras.

We claim:

1. A mascara composition comprising a seedless, unfiltered whole processed fruit or vegetable extract of at least tacky constituents of the fruit or vegetable selected from the group consisting of whole pulp and skin dispersed in a silicone oil.

2. The composition of claim 1 in which said whole processed fruit or vegetable extract is present in an amount of about 0.05 to about 0.50 percent by weight of the composition.

3. The composition of claim 2 in which said whole processed fruit or vegetable extract is present in an amount of about 0.1 to about 0.4 percent by weight of the composition.

4. The composition of claim 1 in which said whole processed fruit is fruit-derived.

5. The composition of claim 4 in which said fruit is selected from the group consisting of apple, pear, peach, mango, papaya, apricot, nectarine and combinations thereof.

6. The composition of claim 5 in which said fruit is apple.

7. The composition of claim 1 in which said vegetable extract is vegetable-derived.

8. The composition of claim 7 in which said vegetable is selected from the group consisting of yams, potatoes, peas, peppers, beans, squashes, carrots, and combinations thereof.

9. The composition f claim 1 in which said silicone oil is volatile.

10. The composition of claim 9 in which said volatile oil is selected from the group consisting of cyclomethicone, hexamethylcyclotrisiloxane, octarnethylcyclotetrasiloxane, decarnethylcyclopentasiloxane, and dimethylpolysiloxane.

11. The composition of claim 10 in which said silicone oil is cyclomethicone.

12. The composition of claim 1 in which said silicone oil is non-volatile.

13. The composition of claim 12 in which said non-volatile oil is selected from the group consisting of dimethicone, cetyl dimethicone, phenyl trimethicone, lauryl trimethicone, dimethiconol, and mixtures thereof.

14. The composition of claim 1 wherein said whole processed fruit or vegetable extract comprises natural fibers.

15. The composition of claim 14 further comprising non-plant fibers selected from the group consisting of synthetic non-plant fibers and natural non-plant fibers.

16. The composition of claim 15 in which said non-plant fiber is synthetic.

17. The composition of claim 16 in which said synthetic fiber is selected from the group consisting of polyester, polyethylene, polypropylene, acrylic, aramid, rayon, cotton, wool, silk, nylon and blends fiber.

18. The composition of claim 15 in which said non-plant fiber is natural.

19. The composition of claim 18 in which said natural non-plant fiber is selected from the group consisting of chitin, etherified chitin, esterified chitin, chitosan, quaternary chitosan, and derivatives thereof.

20. The composition of claim 15 further comprising an antistatic agent present in an amount of about 0.01 to about 10.00 percent by weight of the composition.

21. The composition of claim 20 in which said antistatic component is selected from the group consisting of nonionic, anionic, cationic, and amphoteric surfactants; ammo sugars; and mixtures thereof.

22. The composition of claim 21 in which said amino sugar is chitin.

23. The composition of claim 1 which also comprises a pigment.

24. A mascara composition comprising a seedless unfiltered whole processed fruit or vegetable extract of at least tacky constituents of the fruit or vegetable selected from the group consisting of whole pulp and skin dispersed in a volatile silicone oil, an antistatic component, a non-plant fiber component, and said whole processed fruit or vegetable extract comprising a natural fiber component.

25. The composition of claim 24 in which said whole processed fruit is apple-derived.

26. The composition of claim 25 in which said non-plant fiber component is nylon.

27. The composition of claim 26 in which said antistatic component is chitin.

28. The composition of claim 27 in which said non-plant fiber component further comprises chitin.

29. A mascara composition for application to the eyelashes comprising about 0.05 to about 0.50 percent by weight of the composition of a seedless unfiltered whole processed apple extract of at least tacky constituents of the apple extract selected from the group consisting of whole pulp and skin dispersed in a cyclomethicone, a non-plant fiber component comprising nylon and chitin, an antistatic component comprising chitin, and said whole processed apple extract comprising a natural apple fiber component.

* * * * *